(12) United States Patent
Stährfeldt

(10) Patent No.: US 6,172,232 B1
(45) Date of Patent: Jan. 9, 2001

(54) LIGHT STABILIZERS BASED ON STERICALLY HINDERED AMINES

(75) Inventor: Thomas Stährfeldt, Neusäss (DE)

(73) Assignee: Clariant GmbH, Frankfurt (DE)

( * ) Notice: Under 35 U.S.C. 154(b), the term of this patent shall be extended for 0 days.

(21) Appl. No.: 09/146,610

(22) Filed: Sep. 3, 1998

(30) Foreign Application Priority Data

Sep. 4, 1997 (DE) .............................. 197 38 615

(51) Int. Cl.[7] .................... C07D 215/16; C07D 215/20; C07D 216/36
(52) U.S. Cl. .................... 546/155; 546/156; 546/157
(58) Field of Search .................... 546/155, 156, 546/157

(56) References Cited

U.S. PATENT DOCUMENTS

| | | | |
|---|---|---|---|
| 4,035,423 | 7/1977 | Gallay et al. | 260/571 |
| 4,289,686 | 9/1981 | Rody et al. | 260/45.8 |
| 4,314,933 | 2/1982 | Berner | 260/45.75 |
| 4,481,315 | 11/1984 | Rody et al. | 524/89 |
| 5,705,545 | 1/1998 | Avar et al. | 524/102 |
| 5,753,729 | 5/1998 | Valet et al. | 524/100 |

FOREIGN PATENT DOCUMENTS

| | | |
|---|---|---|
| 2431584 | 1/1975 | (DE) . |
| 4327297 | 2/1994 | (DE) . |
| 4416809 | 11/1994 | (DE) . |
| 198 20 157 | 11/1998 | (DE) . |
| 0010516 | 4/1980 | (EP) . |
| 0016723 | 10/1980 | (EP) . |
| 0200190 | 11/1986 | (EP) . |
| 0389427 | 9/1990 | (EP) . |
| 0575835 | 12/1993 | (EP) . |
| 0593936 | 4/1994 | (EP) . |
| 0640591 | 3/1995 | (EP) . |
| wo 97/42171 | 11/1997 | (WO) . |

OTHER PUBLICATIONS

XP 002087679 & JP 50 159483 A (Kyodo Chem Co Ltd) Dec. 24, 1975.
R. Gächter, H. Müller, Plastic Additives Handbook, 3rd Ed., Hanser Verlag, Munich 1990, p. 133 ff. & p. 181 ff.
"Coccidiostatisch Wirksame 4–Hydroxy–7–aminomethyl–6–äthylchinolin–3–carbonsäureäthylester," B.E. Schroetter, A. Raddatz, D. Hübler, and K.H. Chemnitius, Pharmazie (1977), 32(4), pp. 223–225.
Organic Snytheses, Collective vol. 3, John Wiley & Sons, Inc., New York, p. 274, 1955.
Hetarene II, Part 1, vol. E7a, p. 343, 1991.
"The Synthesis of 3.3–Diacyl–2–phenylaminoacrylo–nitriles by a Simple Sulphur–Extrusion Reaction," S.E.J. Glue,. I.T. Kay (1977), p. 607.

*Primary Examiner*—D. Margaret Seaman
(74) *Attorney, Agent, or Firm*—Susan S. Jackson; Scott E. Hanf

(57) ABSTRACT

The present invention relates to novel compounds of the formula (I)

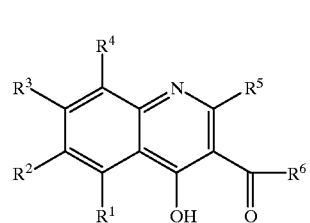

in which the substituents have the meaning defined in the description.

These novel compounds are excellent stabilizers for organic material against the damaging effects of light, heat and oxygen.

1 Claim, No Drawings

LIGHT STABILIZERS BASED ON STERICALLY HINDERED AMINES

BACKGROUND OF THE INVENTION

It is known that organic materials are damaged by light, radiation, heat or oxygen. There are already numerous documents which describe compounds for stabilizing organic material against these effects. The majority of such compounds are free-radical scavengers, hydroperoxide destroyers, quenchers (extinguishers for excited states) or UV absorbers (cf. R. Gächter, H. Müller, Plastics Additives Handbook, 3rd Ed., Hanser Verlag, Munich 1990, p. 133 ff.). In the context of UV absorbers, the compounds generally involved are based on 2-hydroxybenzophenone, 2-hydroxyphenyl-benzotriazole, cinnamic esters and oxanilides (cf. R. Gächter, H. Müller, Plastics Additives Handbook, 3rd Ed., Hanser Verlag, Munich 1990, p. 181 ff.). The class of the o-hydroxy-substituted triphenylpyrimidines can be regarded as a relatively new type of UV stabilizer (DE-A-4416809).

Said classes of compound often have specific disadvantages which occur alongside the desired stabilizing effect. Especially in respect of color behavior, interaction with pigments, compatibility of different, simultaneously employed stabilizers with one another and with the material to be stabilized, resistance to chemicals and water (sensitivity to hydrolysis), storage stability, migration behavior and improvement of stabilization against the damaging effects of heat and light in long-term use, there is a great need for new classes of stabilizer.

Derivatives of 4-hydroxyquinoline-3-carboxylic acid, especially the free acid and the methyl and ethyl esters, have been known for some time in connection with pharmaceutical applications (cf. e.g. B. E. Schroetter et al, Pharmazie (1977), 32(4), 223–5).

The applications known to date relate to the action of 4-hydroxyquinoline-3-carboxylic acid and its esters against bacteria, parasites, tumors, suppurating ulcers, gastrointestinal dysfunctions and as enzyme inhibitors. Derivatives of 4-hydroxyquinoline-3-carboxylic acid are not known for their UV-stabilizing action. Substances which combine a UV stabilizer and a sterically hindered amine simultaneously in the molecule can be particularly effective light stabilizers. In this context, for example, UV absorbers based on 2-hydroxy-benzophenone, on 2-hydroxyphenylbenzotriazole and on cinnamic acids are encountered. This is known, inter alia, from EP-A-389 427; EP-A-10 516; EP-A-16 723; EP-A-200 190; EP-A-593 936; DE-A-4 327 297.

SUMMARY OF THE INVENTION

It has now surprisingly been found that compounds which combine a 4-hydroxyquinoline-3-carboxylic acid derivative and a sterically hindered amine simultaneously in the molecule in the manner shown in formula (I) have an excellent protective effect for organic material against the damaging effects of light, heat and oxygen. In the near UV region, which is of interest, the substances (I) generally possess extinction coefficients of from 10,000 to 15,000 (see Experimental Section).

DESCRIPTION OF THE PREFERRED EMBODIMENT

The present application therefore provides novel compounds of the formula (I)

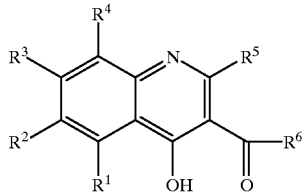

(I)

In this formula $R^1$ to $R^4$ independently of one another are halogen, H, $NO_2$, $CF_3$, CN; $C_1$–$C_{20}$-, preferably $C_1$–$C_{10}$-, especially $C_1$–$C_4$-alkyl, - S-alkyl or —O-alkyl; $C_6$–$C_{14}$-, preferably $C_6$–$C_{10}$-aryl, —S-aryl or —O-aryl; $C_5$–$C_{13}$-, preferably $C_5$–$C_{10}$-heteroaryl; $C_7$–$C_{26}$-, preferably $C_7$–$C_{13}$-alkylaryl, —S-alkylaryl or —O-alkylaryl.

Two of the radicals $R^1$ to $R^4$ may together with the parent structure form a 5- to 12-membered, preferably a 5- or 6-membered aliphatic ring which is unsubstituted or substituted by halogen, $NO_2$, CN, $CF_3$, $C_1$–$C_{20}$-, preferably $C_1$–$C_{10}$-, especially $C_1$–$C_4$-alkyl, —O-alkyl or —S-alkyl, $C_6$–$C_{14}$-, preferably $C_6$–$C_{10}$-aryl, —O-aryl or —S-aryl, $C_5$–$C_{13}$-, preferably $C_5$–$C_{10}$-heteroaryl, $C_7$–$C_{26}$-, preferably $C_7$–$C_{13}$-alkylaryl, —O-alkylaryl or —S-alkylaryl and can include one or more heteroatoms; this aliphatic ring can in particular be interrupted by —S—, —O—, —N(H)—.

Of the radicals $R^1$ to $R^4$, two adjacent radicals in each case may together with the parent structure form a further 5- or 6-membered, preferably 6-membered aromatic ring which is unsubstituted or substituted by halogen, $NO_2$, $CF_3$, CN, $C_1$–$C_{20}$-, preferably $C_1$–$C_{10}$-, especially $C_1$–$C_4$-alkyl, —O-alkyl or —S-alkyl, $C_6$–$C_{14}$-, preferably $C_6$–$C_{10}$-aryl, —O-aryl or —S-aryl, $C_5$–$C_{13}$-, preferably $C_5$–$C_{10}$-heteroaryl, $C_7$–$C_{26}$-, preferably $C_7$–$C_{13}$-alkylaryl, —O-alkylaryl or —S-alkylaryl and can include one or more heteroatoms, or can be fused with a further aromatic nucleus.

$R^5$ is H, CN or $SR^7$.

$R^7$ is H; $C_1$–$C_{20}$-alkyl which is unsubstituted or substituted by halogen, $NO_2$, CN, $CF_3$, $C_1$–$C_{20}$-, preferably $C_1$–$C_4$-O-alkyl, $C_6$–$C_{14}$-, preferably $C_6$–$C_{10}$-aryl, O-$C_6$–$C_{20}$-, preferably O-$C_6$–$C_{10}$-aryl or O-$C_7$–$C_{26}$-, preferably O-$C_7$–$C_{13}$-arylalkyl; preferably an unsubstituted $C_1$–$C_{10}$-alkyl, especially methyl; or $C_6$–$C_{14}$-aryl which is unsubstituted or substituted by halogen, $NO_2$, CN, $CF_3$, O-$C_1$–$C_{20}$-, preferably O-$C_1$–$C_{10}$-, especially O-$C_1$–$C_4$-alkyl, O-$C_6$–$C_{14}$-, preferably O-$C_6$–$C_{10}$-aryl, or O-$C_7$–$C_{26}$-, preferably O-$C_7$–$C_{13}$-arylalkyl;

$R^6$ is

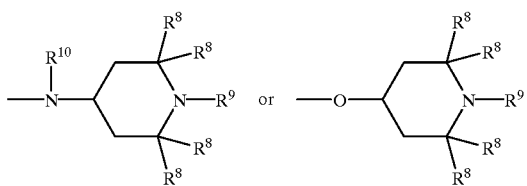

$R^8$ is hydrogen or a $C_1$–$C_{12}$-alkyl group, preferably a $C_1$–$C_4$-alkyl group, especially a methyl group;

$R^9$ is hydrogen or a $C_1$–$C_{22}$-, preferably a $C_1$–$C_5$-alkyl group, especially a methyl group, an oxygen radical O*, —OH, —NO, —CH$_2$CN, benzyl, allyl, a $C_1$–$C_{30}$-, preferably a $C_1$–$C_{10}$-alkyloxy group, a $C_5$–$C_{12}$-, preferably a $C_5$–$C_6$-cycloalkyloxy group, a $C_6$–$C_{10}$-, preferably a $C_6$–$C_7$-, especially a $C_6$-aryloxy group, where the aryl radical can additionally be substituted; a $C_7$–$C_{20}$-, preferably a $C_7$–$C_{10}$-arylalkyloxy group, where the aryl radical can additionally be substituted, a $C_3$–$C_{10}$-, preferably a $C_3$–$C_6$-alkenyl group, a $C_3$–$C_6$-alkynyl group, a $C_1$–$C_{10}$-, preferably a $C_1$–$C_5$-acyl group, halogen, or a phenyl radical which is unsubstituted or substituted by $C_1$–$C_4$-, preferably by $C_1$–$C_2$-alkyl, $R^{10}$ is hydrogen or $C_1$–$C_{12}$-alkyl group, preferably a $C_1$–$C_4$-alkyl group, especially a butyl group.

The 4-hydroxyquinoline-3-carboxylic esters, in other words the precursors of the compounds (I) of the invention, can be prepared in accordance with the prior art, especially by the method described, inter alia, in Organic Syntheses Coll. Vol. III, p. 274 and in Houben-Weyl, Heterarene II, Part 1, Volume E7a, p. 343 ff., by the thermal cyclization of appropriately substituted dialkyl(arylamino-methylene) malonates in a high-boiling solvent. These precursors can also be prepared by the methods described in DE-A-2 431 584. The cyclizable dialkyl S-alkyl-substituted (arylamino-methylene)malonates for the synthesis of 4-hydroxyquinoline-3-carboxylic esters having the —S-alkyl substituent, especially the —S-CH$_3$-substituent, in position 2 can be prepared in analogy to the method published in Houben-Weyl, Heterarene II, Part 1, Volume E7a, p. 376, especially by reaction of aryl thioisocyanate with the sodium salt of malonic acid and subsequent reaction with alkyl iodide. The precursor for the derivatives having the —CN substituent in position 2 can be prepared by the method described by S. E. J. Glue, I. T. Kay in Synthesis (1977), 607–8.

The cyclizations of these precursors to give the compounds of the invention can be conducted in a high-boiling organic solvent, especially in boiling o-dichlorophenol or in boiling diphenyl ether.

The preparation of the substances of the invention has not been described to date. The novel substances (I) can be prepared by a transesterification starting from a 4-hydroxyquinoline-3-carboxylic ester and an appropriately substituted sterically hindered amine, especially by transesterification with 2,2,6,6-tetramethylpiperidin-4-ol, 2,2,6,6-tetramethylpiperidine-4-amine or N-butyl-2,2,6,6-tetramethylpiperidine-4-amine. A transesterification of this kind can be conducted in an organic solvent, preferably in an aromatic solvent, especially in xylene.

The transesterification is particularly successful if the mixture of the starting materials additionally has a catalyst added to it. Examples of suitable catalysts are amides of metals of the first main group of the Periodic Table and organometallic compounds and oxides of metals of the fourth main group or of the fourth subgroup of the Periodic Table. Suitable amides are compounds of the formula MNH$_2$ where M=Li, Na. Examples of metal oxides in this context are germanium dioxide or zirconium dioxide.

Suitable organometallic compounds of metals of the fourth main group or of the fourth subgroup of the Periodic Table are, for example, compounds of the formula M'(OR$^{11}$)$_4$, in which R$^{11}$ can be alkyl, phenyl or benzyl and M' can be the element Ge, Zr, Sn or Ti. Also suitable are compounds of the formula (R$^{12}$)$_2$SnO, where R$^{12}$ is a $C_4$–$C_{20}$-alkyl. Particularly suitable catalysts are lithium amide, dialkyltin oxides or tetraalkyl orthotitanates, especially di-n-butyltin oxide, tetrabutyl orthotitanate and tetraisopropyl orthotitanate.

The novel light stabilizers of the formula (I) can be added in solid form, as a melt or else dissolved in solvents, or as a masterbatch, to the organic material to be stabilized, prior to, during or after the polymerization. When added as a solid, the compounds of the formula (I) in finely divided form are particularly suitable. A masterbatch is particularly suitable if it comprises the novel stabilizer in a concentration of from 1 to 80%, but preferably 5–30% by weight, the remainder of the masterbatch comprising a polymer which is compatible with the polymer to be stabilized. Incorporation in dissolved form is particularly appropriate, in which case the solutions can comprise the novel stabilizer, for example, in a concentration of 5–80% by weight. Both the solution and the masterbatch may contain, in addition, further stabilizers or effect substances, examples being further UV absorbers, light stabilizers based on sterically hindered amines, quenchers, antioxidants, pigments, acid scavengers or fillers. The novel stabilizers are preferably employed such that they are present in a concentration of from 0.001 to 5% by weight, preferably from 0.02 to 2% by weight, based on the organic material, in the polymer to be stabilized, and are present either alone or in combination with further additives. By organic material is meant, for example, precursors of plastics, paints, varnishes and oils, but especially plastics, paints, varnishes and oils themselves.

The stabilizers of the formula (I) are particularly suitable for stabilizing films, fibers, tapes, multifilaments, wovens, extruded, blow molded, injection molded and thermoformed articles, powder coating materials, printing inks, toner inks, photographic material, pigments, wood stains, leathers, architectural paints, protective coatings for steel structures, lubricating oils, machine oils, bitumen, asphalt, and cosmetic or pharmaceutical applications, in which the stabilizing nature, and in particular the UV-absorbing nature, of the compounds of the formula (I) is of advantage.

The stabilizers of the formula (I) according to the invention can also be employed advantageously in combination with other stabilizers. The result of these new combinations are mixtures having an improved profile of properties relative to the individual components, such as, for example, synergistic photoprotective effects.

The present invention additionally provides an organic material stabilized against the effects of light, oxygen and heat, especially plastics, paints, varnishes and oils, which comprises compounds of the formula (I) in the concentrations stated above.

Examples of such materials are described in German Patent Application No. 19 719 944.5 on pages 44 to 50, the content of which is expressly incorporated herein by reference.

The organic material stabilized by the compounds of the formula (I) according to the invention or by an appropriate combination comprising such a compound may additionally include further additives, if desired, examples being antioxidants, light stabilizers, metal deactivators, antistatic agents, flame retardants, lubricants, nucleating agents, acid scavengers, (basic costabilizers), pigments and fillers. Antioxidants and light stabilizers which are added in addition to the compounds or combinations of the invention are, for example, compounds based on sterically hindered amines or sterically hindered phenols, or sulfur- or phosphorus-containing costabilizers.

EXPERIMENTAL SECTION

General preliminary remarks on preparing the novel light stabilizers

The precursors (ethyl 4-hydroxyquinoline-3-carboxylates) of the compounds 1 to 18 employed in accordance with the invention were prepared in accordance with the prior art, in particular by the methods described inter alia in Organic Syntheses, Coll. Vol. III, p. 274 and in Houben-Weyl, Heterarene II, Part 1, Volume E7a, p. 343 ff., in other words, by the thermal cyclization of appropriately substituted dialkyl(arylaminomethylene)malonates in a high-boiling solvent (diphenyl ether, 50 minutes). The cyclizable dialkyl(arylamino-methylene)malonates acid were prepared by condensing primary amines with dialkyl ethoxymethylene-malonates, as described in Houben-Weyl, Heterarene II, Part 1, Volume E7a, p. 345.

The precursors of 4-hydroxyquinoline-3-carboxylic esters with the —S-CH₃ substituent in position 2 were prepared in analogy to the method published in Houben-Weyl, Heterarene II, Part 1, Volume E7a, p. 376 ff., phenyl isothiocyanate being reacted with the sodium salt of diethyl malonate to give the corresponding diethyl (phenylaminomethylene) malonate thiolate, which was reacted with methyl iodide to give the S-methyl compound. The cyclization of this precursor to give the 4-hydroxyquinoline-3-carboxylic ester was carried out thermally in diphenyl ether with a yield of about 70%. The precursors for the derivatives with the —CN substituent in position 2 were prepared by the method described by S. E. J. Glue, I. T. Kay in Synthesis (1977), 607–8 and were cyclized in boiling o-dichlorobenzene in a yield of 23%.

EXAMPLES 1–18

Preparing compounds 1–18

0.05 mol of a 4-hydroxyquinoline-3-carboxylic ester substituted appropriately on the aromatic parent structure is stirred at 136° C. together with 0.055 mol of a 2,2,6,6-tetramethylpiperidine derivative with appropriate substitution in position 4 (4-hydroxy-2,2,6,6-tetramethylpiperidine, 4-amino-2,2,6,6-tetramethylpiperidine or N-butyl-2,2,6,6-tetramethyl-4-piperidine) and 0.2 g of di-n-butyltin oxide in 300 ml of xylene. The ethanol which forms is distilled off successively together with a small amount of xylene via a Vigreux column. When TLC indicates the end of the reaction (about 48 h), the entire reaction mixture is mixed thoroughly with 300 ml of water. The precipitate which forms is filtered off with suction and the crude product thus isolated is recrystallized from DMF. The yield and characterization of the corresponding compounds are shown in Tables 1–4.

TABLE 1

Examples 1–9:
4-hydroxyquinoline-3-carboxylic acid derivatives of 4-amino-2,2,6,6-tetramethylpiperidine

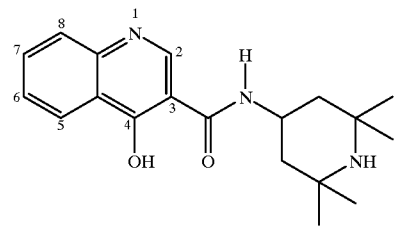

| Example No. | Radical | Yield | m.p. | UV spectrum | Extinction coefficient |
|---|---|---|---|---|---|
| 1 | 6-F | 82.7% | 295° C. (d.) | 302 (vs)* | 8656 |
| | | | | 321 (vs)* | 8848 |
| | | | | 334 (s)* | 7051 |
| 2 | 8-Cl | 59.6% | 177° C. (d.) | 308 (s,sh)* | — |
| | | | | 322 (vs)* | 11721 |
| | | | | 333 (vs)* | 12264 |
| 3 | 6-CF₃ | 50.4% | 266° C. (d.) | 306 (s,sh)# | — |
| | | | | 315 (vs)# | 13010 |
| | | | | 328 (s,sh)# | — |
| 3 | 6-CF₃ | 50.4% | 266° C. (d.) | 247 (s)$ | 13401 |
| | | | | 255 (vs)$ | 15786 |
| | | | | 313 (vs)$ | 11608 |
| 4 | 8-CF₃ | 77.3% | 279° C. | 305 (w,sh)* | — |
| | | | | 325 (s,sh)* | — |
| | | | | 334 (vs)* | 10518 |
| 5 | 8-Φ | 78.5% | 267° C. | 309 (s,sh)* | — |
| | | | | 321 (vs)* | 12179 |
| | | | | 331 (s)* | — |
| 5 | 8-Φ | 78.5% | 267° C. | 230 (vs)$ | 36639 |
| | | | | 313 (s)$ | 15168 |
| | | | | 328 (m,sh)$ | — |
| 6 | 7-OCH₃ | 54.7% | 318° C. (d.) | 298 (m,sh)* | — |
| | | | | 309 (vs)* | 10370 |
| | | | | 321 (vs)* | 11109 |
| 7 | 6-OCH₂Φ | 69.0% | 78° C. | 307 (vs)* | 9692 |
| | | | | 328 (s)* | 7621 |
| | | | | 343 (m)* | 6013 |
| 7 | 6-OCH₂Φ | 69.0% | 78° C. | 253 (vs)$ | 25702 |
| | | | | 262 (vs)$ | 25248 |
| | | | | 307 (s)$ | 10165 |
| | | | | 327 (m)$ | 7748 |
| | | | | 342 (m)$ | 5537 |
| 8 | 8-S—CH₃ | 62.5% | 261° C. | 315 (s,sh)* | — |
| | | | | 327 (vs)* | 11813 |
| | | | | 335 (s,sh)* | 11557 |
| 9 | 2-S—CH₃ | 79.5% | 160° C. | 307 (s)* | 7400 |
| | | | | 320 (vs)* | 7683 |
| | | | | 348 (m)* | — |
| 9 | 2-S—CH₃ | 79.5% | 160° C. | 234 (s)$ | 20374 |
| | | | | 271 (vs)$ | 34860 |
| | | | | 303 (s)$ | 9720 |

(d.) means: decomposition at the stated temperature
*UV spectrum in DMF
UV spectrum in DMSO
$UV spectrum in ethanol
In the description of the UV spectra, vs = very stong, s = strong, m = medium, w = weak, sh = shoulder.

TABLE 2

Examples 10–17:
4-hydroxyquinoline-3-carboxylic acid derivatives of 4-hydroxytriacetonamine (TAA-ol)

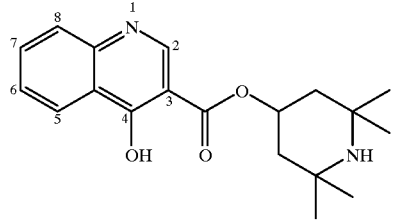

| Example No. | Radical | Yield | m.p. | UV spectrum in ethanol | Extinction Coefficient |
|---|---|---|---|---|---|
| 10 | 8-CH$_3$ | 68.9 | 274° C. (d.) | — | — |
| 11 | 8-Cl | 90.8% | 259° C. | — | — |
| 12 | 6-CF$_3$ | 38.7% | 277° C. (d.) | — | — |
| 13 | 2-S—CH$_3$ | 73.1% | 125° C. | 232 (s) 267 (vs) 323 (m, sh) | — 33967 — |
| 14 | 6-NO$_2$ | 67.9% | >300° C. | — | — |
| 15 | 8-NO$_2$ | 49.1% | 238° C. | — | — |
| 16 | 6-n-Bu | 93.8% | 266° C. | — | — |
| 17 | 6,8-di-Cl | 53.8% | 274° C. (d.) | — | — |

(d.) means: decomposition at the stated temperature

TABLE 3

Example 18:
4-hydroxyquinoline-3-carboxylic acid derivative of N-butyl-2,2,6,6-tetramethyl-4-piperidine

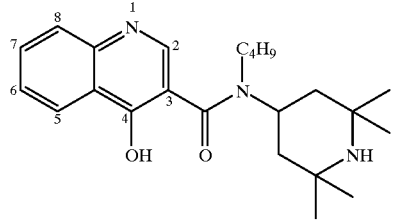

| Example No. | Radical | Yield | m.p. | UV spectrum in ethanol | Extinction Coefficient |
|---|---|---|---|---|---|
| 18 | 2-CH$_3$ | 20.4% | 169° C. | 256 (vs) 265 (vs) 327 (m) | — 17870 9696 |

TABLE 4

Volatilities of some 4-hydroxyquinoline-3-carboxylic acid derivatives

| Product | 2 | 5 | 6 | 14 |
|---|---|---|---|---|
| Volatility | 24% | 19% | 18% | 11% |

To determine the volatility, 500 mg of the respective substance are heated to 300° C. under nitrogen at a rate of 120° C./h and are held at 300° C. for 30 minutes (boat: Pt, surface area: 3 cm$^2$) The table indicates the weight loss after 30 minutes at 300° C.

Examples 19–28

Light stabilizing action in polypropylene films 100 parts by weight of unstabilized polypropylene (®Hostalen PPK) were kneaded in a Brabender mixer at 200° C. and 20 rpm for 5 minutes together with 0.2 part by weight of calcium stearate (from Greven), 0.1 part by weight of tris(2,4-di-tert-butylphenyl) phosphite (®Hostanox PAR 24) and 0.2 part by weight of the stabilizer 2. A 200 µm thick film was pressed from this mixture at 190° C. and the test specimens obtained in this way were exposed in an accelerated weathering device (®Xenotest 1200). The criterion employed for the stability of the film was the change in the carbonyl index. This carbonyl index, CO, was determined in accordance with the formula $CO = E_{1720}/E_{2020}$ (E=extinction). For purposes of comparison, a film was tested under the same conditions but without the addition of a stabilizer of the invention. The test results are summarized in Table 5:

TABLE 5

Change in the carbonyl index of films stabilized in accordance with the invention

| Example No. | Stabilizer | Time after which the carbonyl index has risen by 1 unit (in hours) |
|---|---|---|
| | no stabilizer | 190 h |
| 19 | stabilizer 1 | 380 h |
| 20 | stabilizer 2 | 300 h |
| 21 | stabilizer 3 | 310 h |
| 22 | stabilizer 4 | 330 h |
| 23 | stabilizer 5 | 370 h |
| 24 | stabilizer 8 | 270 h |
| 25 | stabilizer 9 | 300 h |
| 26 | stabilizer 13 | 370 h |

Table 5 emphasizes the photoprotective effect of the stabilizers of the invention.

I claim:

1. A compound of the formula (I),

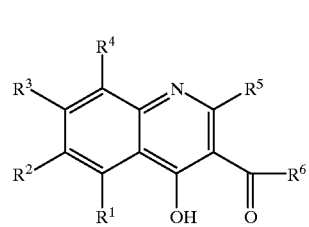

in which

R$^1$ to R$^4$ independently of one another are H, halogen, CF$_3$, NO$_2$, C$_1$–C$_4$-alkyl, S-C$_1$–C$_4$-alkyl, O-C$_1$–C$_6$-alkyl, C$_6$–C$_{10}$-aryl, C$_7$–C$_{13}$-alkylaryl, O-C$_7$–C$_{13}$-alkylaryl, or S-C$_7$–C$_{13}$-alkylaryl, R$^5$ is H or SR$^7$, $R^6$ is one of the following radicals,
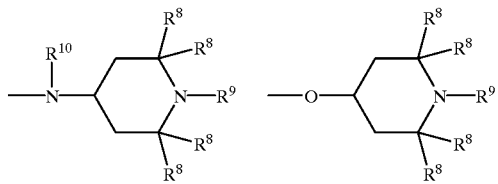
$R^7$ is H, $C_1$–$C_{10}$-alkyl, $C_6$–$C_{14}$-aryl,
$R^8$ is H or methyl,
$R^9$ is H, methyl or a $C_6$-aryloxy group, and
$R^{10}$ is H or a butyl group.
* * * * *